United States Patent

Krummel et al.

[11] Patent Number: 5,808,066
[45] Date of Patent: Sep. 15, 1998

[54] PROCESS FOR THE PREPARATION OF DIHALOAZOLOPYRIMIDINES

[75] Inventors: Günter Krummel, Vendersheim; Karl-Otto Stumm, Aspisheim; Klaus-Jürgen Pees, Mainz; Peter Heinz Rudi Liers, Muenster-Sarmsheim, all of Germany

[73] Assignee: American Cyanamid Company, Madison, N.J.

[21] Appl. No.: 729,204

[22] Filed: Oct. 15, 1996

Related U.S. Application Data

[60] Provisional application No. 60/008,022 Oct. 17, 1995.
[51] Int. Cl.$^6$ ................................................ C07D 487/04
[52] U.S. Cl. ............................................................ 544/263
[58] Field of Search ............................................. 544/263

[56] References Cited

U.S. PATENT DOCUMENTS

| 3,907,799 | 9/1975 | O'Brien et al. | 260/256.4 |
| 5,006,656 | 4/1991 | Shankar et al. | 544/263 |

FOREIGN PATENT DOCUMENTS

| 0 322 359 A2 | 12/1988 | European Pat. Off. . | |
| 550113 | 12/1992 | European Pat. Off. | C07D 487/04 |
| 35 22 463 A1 | 1/1987 | Germany . | |
| WO 95/11246 | 4/1995 | WIPO . | |

OTHER PUBLICATIONS

G. Fisher, Advances in Heterocyclic Chemistry, 1993, 57, 81–138.
Y. Makisumi, Chem. Pharm. Bull., 1961, 9, 801–808.

Primary Examiner—Mukund J. Shah
Assistant Examiner—Bruck Kifle
Attorney, Agent, or Firm—Joseph M. Mazzarese

[57] ABSTRACT

An effective and efficient process for the preparation of a dihaloazolopyrimidine having the structural formula

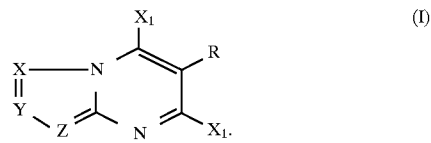

In this process, a malonic acid ester is reacted with a heterocyclylamine to form an intermediate salt, which optionally may be acidified to form a dihydroxyazolopyrimidine; the salt or the dihydroxyazolopyrimidine is then halogenated.

34 Claims, No Drawings

PROCESS FOR THE PREPARATION OF DIHALOAZOLOPYRIMIDINES

This application claims priority from the co-pending provisional application 60/008,022 filed Oct. 17, 1995.

BACKGROUND OF THE INVENTION

Dihaloazolopyrimidines are useful as intermediates in the preparation of a variety of agrochemical and pharmaceutical compounds. In particular, 5,7-dihalo-6-aryl-1,2,4-triazolo[1,5-a]pyrimidines are key intermediates in the preparation of fungicidal triazolopyrimidine derivatives which are described in EP-A2-550113.

EP-A2-550113 describes a method for the preparation of 5,7-dihalo-6-aryl-1,2,4-triazolo[1,5-a]pyrimidines from malonic acid esters and 3-amino-1,2,4-triazole. However, that method is not entirely satisfactory because those pyrimidine compounds are obtained in low yield.

G. Fischer (Advances in Heterocyclic Chemistry, 1993, 57, 81–138) describes the formation of triazolopyrimidines from 1,3-dicarbonyl compounds and 3-amino-1,2,4-triazole, and states that refluxing in glacial acetic acid is "standard conditions". Y. Makisumi (Chem. Pharm. Bull., 1961, 9, 801–808) reports that under those conditions the condensation of diethyl malonate with 3-amino-1,2,4-triazole does not proceed. Makisumi discloses that the reaction could be carried out in the presence of sodium ethoxide in ethanol, and that the product dihydroxytriazolopyrimidine could be converted to the corresponding dichlorotriazolopyrimidine using a large excess of phosphorus oxychloride. However, Makisumi's method is not entirely satisfactory for the preparation of dihaloazolopyrimidines because a large excess of phosphorus oxychloride is required and the overall yield of the reactions starting from diethyl malonate is often low.

SUMMARY OF THE INVENTION

The present invention provides an effective and efficient process for the preparation of a dihaloazolopyrimidine having the structural formula I

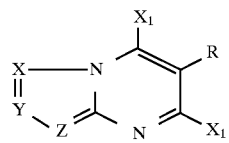

wherein $X_1$ is chlorine or bromine;

R is phenyl optionally substituted with one or more halogen, nitro, cyano, $C_1$–$C_6$alkyl, $C_1$–$C_6$haloalkyl, $C_1$–$C_6$alkoxy, $C_1$–$C_6$haloalkoxy, $C_1$–$C_4$alkoxycarbonyl, phenyl, phenoxy or benzyloxy groups, naphthyl optionally substituted with one or more halogen, nitro, cyano, $C_1$–$C_6$alkyl, $C_1$–$C_6$haloalkyl, $C_1$–$C_6$alkoxy, $C_1$–$C_6$haloalkoxy, $C_1$–$C_4$alkoxycarbonyl, phenyl, phenoxy or benzyloxy groups, hydrogen, $C_1$–$C_6$alkyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, $C_3$–$C_8$cycloalkyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups, or $C_2$–$C_6$alkenyl optionally substituted with one or more halogen, nitro, cyano, $C_1$–$C_4$alkyl, $C_1$–$C_4$haloalkyl, $C_1$–$C_4$alkoxy or $C_1$–$C_4$haloalkoxy groups;

X is $CR_1$ or N;

Y is $CR_2$ or N;

Z is $CR_3$ or N;

$R_1$, $R_2$ and $R_3$ are each independently hydrogen or $C_1$–$C_6$alkyl optionally substituted with one or more halogen, nitro, cyano, $C_1$–$C_4$alkyl, $C_1$–$C_4$haloalkyl, $C_1$–$C_4$alkoxy, $C_1$–$C_4$haloalkoxy, amino, $C_1$–$C_4$alkylamino or di($C_1$–$C_4$alkyl)amino groups, and when $R_1$ and $R_2$ are taken together with the atoms to which they are attached, they may form a ring in which $R_1R_2$ is represented by the structure: —$CR_4$=$CR_5$–$CR_6$=$CR_7$— where $R_4$, $R_5$, $R_6$ and $R_7$ are each independently hydrogen, nitro, cyano, $C_1$–$C_4$alkyl, $C_1$–$C_4$haloalkyl, $C_1$–$C_4$alkoxy or $C_1$–$C_4$haloalkoxy, which process comprises: (a) reacting (1) a malonic acid ester having the structural formula II

wherein $R_8$ and $R_9$ are each independently $C_1$–$C_6$alkyl, and R is as described above with (2) a heterocyclylamine having the structural formula III

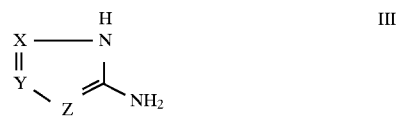

wherein X, Y and Z are as described above at a temperature of at least about 100° C. to form an intermediate salt; (b) optionally acidifying the intermediate salt with aqueous acid to form a dihydroxyazolopyrimidine having the structural formula IV

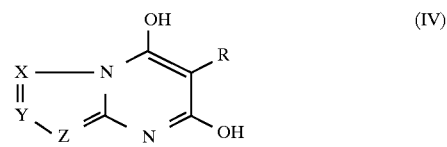

wherein R, X, Y and Z are as described above; and (c) halogenating the intermediate salt or dihydroxyazolopyrimidine with at least about two molar equivalents of a halogenating agent, e.g., phosphorus oxychloride, phosphorus oxybromide, phosphorus pentachloride or phosphorus pentabromide or a suitable mixture thereof at a temperature of at least about 100° C.

The present invention also provides an effective and efficient process for the preparation of a dihydroxyazolopyrimidine having the structural formula IV

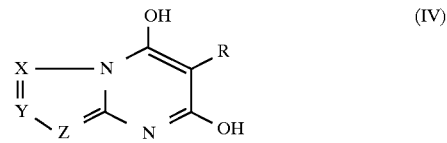

wherein R, X, Y and Z are as described above. This product (IV) is produced by the above-described procedure wherein the intermediate salt is acidified; the product (IV) then may be isolated, if desired.

It is, therefore, an object of the present invention to provide an efficient new process for the preparation of dihaloazolopyrimidines.

It is another object of the present invention to provide a novel process for preparing dihydroxyazolopyrimidines.

Other objects and advantages of the present invention will be apparent to those skilled in the art from the following description and the appended claims.

DETAILED DESCRIPTION OF THE INVENTION

In one preferred embodiment of the present invention, a malonic acid ester represented by formula II is reacted with at least about one molar equivalent of a heterocyclylamine represented by formula III, preferably in a temperature range of about 120° C. to 200° C., more preferably about 150° C. to 180° C., and optionally in the presence of a base and/or solvent to form an intermediate salt. The intermediate salt is halogenated with at least about two molar equivalents of phosphorus oxychloride, phosphorus oxybromide, phosphorus pentachloride or phosphorus pentabromide, or a suitable mixture thereof, preferably in a temperature range of about 120° C. to 150° C.

Advantageously, it has now been found that dihaloazolopyrimidines may be obtained in high yield and good purity by the effective and efficient process of the present invention. In contrast, dihaloazolopyrimidines are obtained in comparatively low yield when prepared according to art methods.

A further advantage of the present invention is that the inventive process may be conducted in one pot when the intermediate salt is not acidified. A one pot reaction sequence is highly desirable because it avoids the isolation of intermediate compounds and significantly reduces the amount of chemical waste produced.

In another preferred embodiment of the present invention, the intermediate salt is prepared in the presence of added base. The base is preferably present in an amount of at least about one molar equivalent relative to the malonic acid ester. Bases suitable for use in the process of the present invention include tertiary amines such as tri($C_2$–$C_6$alkyl)amines, pyridine, substituted pyridines, quinoline, substituted quinolines, and ureas; alkali metal hydroxides such as sodium hydroxide and potassium hydroxide; alkaline earth metal hydroxides such as calcium hydroxide and magnesium hydroxide; alkali metal $C_1$–$C_6$alkoxides such as sodium ethoxide and potassium tert-butoxide; alkaline earth metal $C_1$–$C_6$alkoxides such as magnesium ethoxide; alkali metal carbonates such as sodium carbonate and potassium carbonate; and alkaline earth metal carbonates such as calcium carbonate. Preferred bases include tri($C_2$–$C_6$alkyl)amines such as triethylamine and tributylamine, pyridine, 4-(N,N-dimethylamino)pyridine, quinoline, and N,N,N',N'-tetramethylurea with triethylamine and tributylamine being more preferred.

The intermediate salt of this invention is represented by structural formula V when prepared in the absence of added base, and structural formula VI when prepared in the presence of added base:

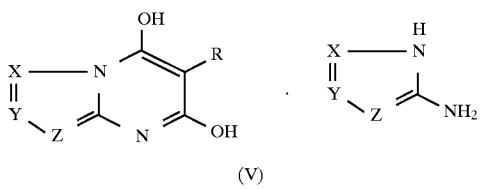

(V)

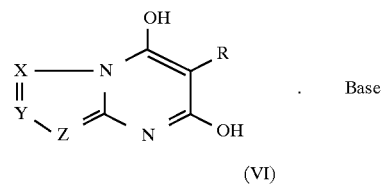

(VI)

wherein R, X, Y and Z are as described above and "Base" represents the added base.

In a further preferred embodiment of the present invention, a solvent is present. Solvents suitable for use in the process of the present invention have a boiling point of at least about 80° C. and include aromatic hydrocarbons such as mesitylene, toluene, xylenes and mixtures thereof; chlorinated aromatic hydrocarbons such as mono- and dihalobenzenes and mixtures thereof; polynuclear aromatic hydrcarbons such as naphthalene, alkylnaphthalenes and mixtures thereof; alcohols such as butanol; and mixtures thereof. The solvent of the present invention preferably has a boiling point range of about 80° C. to 220° C., more preferably about 120° C. to 180° C. Mesitylene is one of the preferred solvents of the present invention.

The reaction between the malonic acid ester and the hetercyclylamine is preferably performed at a pressure of about one atmosphere or higher. If the reaction includes a solvent having a boiling point (defined at normal atmospheric pressure) lower than the reaction temperature, the reaction pressure must be elevated so that the solvent boiling point is elevated to at least the reaction temperature.

In some embodiments of the inventive process, an aqueous acid is used to acidify the intermediate salt. Aqueous acids suitable for use include aqueous mineral acids such as hydrochloric acid, hydrobromic acid and sulfuric acid, and aqueous organic acids such as trifluoroacetic acid with hydrochloric acid, hydrobromic acid, and sulfuric acid being preferred.

The halogenation reaction may comprise reacting the intermediate salt or the dihydroxyazolopyrimidine with a suitable halogenating agent under conditions that produce the desired dihaloazolopyrimidine. Any halogenating agent and conditions known in the art may be used. Preferably, the halogenating agent and conditions are those described herein for the preferred embodiments of the present invention. Advantageously, the halogenation reaction may be conducted at atmospheric pressure or at a pressure greater than atmospheric pressure. The term "a suitable mixture thereof", as used in the specification and claims with regard to the halogenating agents described herein, is defined as a phosphorus oxychloride and phosphorus pentachloride mixture or a phosphorus oxybromide and phosphorus pentabromide mixture.

The process of the present invention is especially useful for the preparation of dihaloazolopyrimidines wherein $X_1$ is chlorine;

R is phenyl optionally substituted with one or more halogen, $C_1$–$C_4$alkyl, $C_1$–$C_4$haloalkyl, $C_1$–$C_4$alkoxy, $C_1$–$C_4$haloalkoxy, phenyl, phenoxy or benzyloxy groups, or naphthyl;

X is $CR_1$ or N;

Y is $CR_2$;

Z is N; and $R_1$ and $R_2$ are each independently hydrogen, and when $R_1$ and $R_2$ are taken together with the atoms to which they are attached, they may form a ring in which $R_1R_2$ is represented by the structure: —CH═CH—CH═CH—.

Advantageously, the present invention is particularly useful for the preparation of 5,7-dihalo-6-aryl-1,2,4-triazolo[1,5-a]pyrimidines of formula I wherein $X_1$ is chlorine;

R is phenyl optionally substituted with one or more halogen, $C_1$–$C_4$alkyl, $C_1$–$C_4$haloalkyl, $C_1$–$C_4$alkoxy or $C_1$–$C_4$haloalkoxy groups;

X and Z are N; and

Y is CH.

The process of the present invention can produce surprisingly high yields of dihydroxyazolopyrimidines and dihaloazolopyrimidines. One key factor is the temperature of the reaction between the malonic acid ester and the heterocyclylamine. The use of a base and/or solvent may also enhance the yield in some embodiments. Those skilled in the art will be able, without undue experimentation, to select a favorable combination of temperature and optional base and/or solvent for any particular embodiment within the scope of this invention, upon consideration of the foregoing description of the preferred embodiments and the Examples that follow.

In order to facilitate a further understanding of the invention, the following illustrative examples are presented. The invention is not limited to the specific embodiments described or illustrated, but encompasses the full scope of the appended claims.

EXAMPLE 1

Preparation of 5,7-Dihydroxy-6-(2-chloro-6-fluorophenyl)-1,2,4-triazolo[1,5-a]pyrimidine, 3-amino-1,2,4-triazole salt

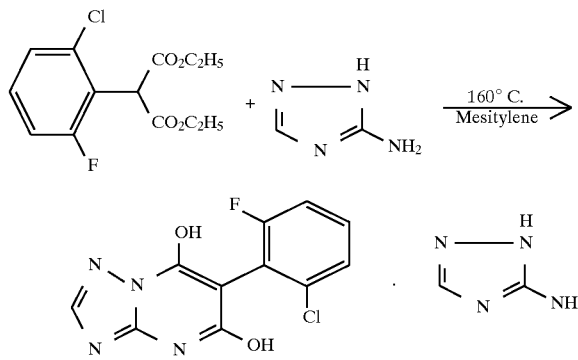

A mixture of diethyl (2-chloro-6-fluorophenyl)malonate (29 g, 0.1 mol), 3-amino-1,2,4-triazole (8.4 g, 0.1 mol), and the solvent mesitylene (10 mL) is heated at 160° C. for 7 hours and filtered to obtain a solid. The solid is washed with diisopropyl ether and dried to give the title product as a solid (18 g, 50% yield, mp 260°–266° C.).

Following essentially the same procedure, but using the appropriate solvent and/or base, the 5,7-dihydroxy-6-(2-chloro-6-fluorophenyl)-1,2,4-triazolo[1,5-a]pyrimidine salts shown in Table I are obtained.

TABLE I

| Solvent | Base | Temperature °C. | % Yield | Salt |
|---|---|---|---|---|
| mesitylene | no added base | 160 | 50 | 3-amino-1,2,4-triazole |
| mesitylene | triethylamine | 160 | 32 | triethylamine |
| SHELLSOL ® | no added base | 180 | 48 | 3-amino-1,2,4-triazole |
| toluene | triethylamine | 170 | 64 | triethylamine |
| no added solvent | triethylamine | 160 | 64 | triethylamine |
| no added solvent | quinoline | 180 | 20 | quinoline |

EXAMPLE 2

Preparation of 5,7-Dichloro-6-(2-chloro-6-fluorophenyl)-1,2,4-triazolo[1,5-a]-pyrimidine

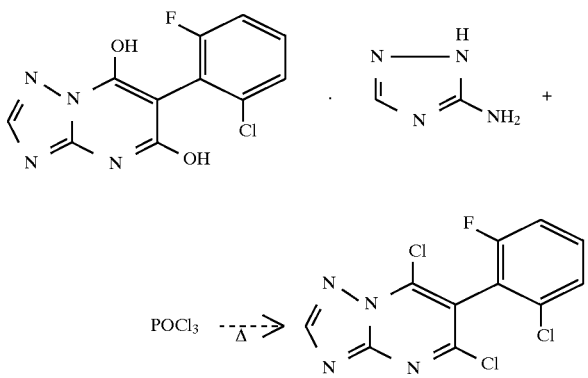

A mixture of 5,7-dihydroxy-6-(2-chloro-6-fluorophenyl)-1,2,4-triazolo[1,5-a]pyrimidine, 3-amino-1,2,4-triazole salt (34.8 g, 0.095 mol), and phosphorus oxychloride (100 mL) is heated in an autoclave at 140° C. (2.8 bar) for 4 hours and excess phosphorus oxychloride is removed by distillation. The resultant reaction mixture is cooled to room temperature and poured into a water/dichloromethane mixture (300 mL, 1:1) while maintaining the temperature of the mixture below 30° C. The organic phase is separated, dried over anhydrous sodium sulfate, and concentrated in vacuo to obtain an oil which crystallizes overnight to give the title product as a solid (22.4 g, 74% yield, mp 118°–120° C.).

EXAMPLE 3

Preparation of 5,7-Dichloro-6-(2-chloro-6-fluorophenyl)-1,2,4-triazolo[1,5-a]-pyrimidine

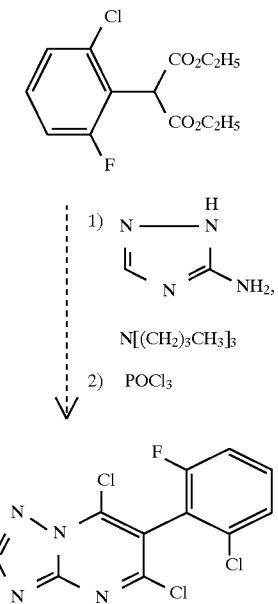

A mixture of 3-amino-1,2,4-triazole (12.6 g, 0.15 mol), diethyl (2-chloro-6-fluorophenyl)malonate (47.6 g, 0.15 mol), and tributyl amine (27.8 g, 0.15 mol) is heated at 170° C. while allowing ethanol generated during the reaction to distill off. After 2 hours, residual ethanol is removed with a slow nitrogen stream for 30 minutes. The reaction mixture is then cooled to 130° C. and phosphorus oxychloride (69 g, 0.45 mol) is added dropwise over 20 minutes. The resultant clear, brown solution is refluxed for 6 hours, cooled to room temperature, and slowly added to a toluene/water (5:6) mixture (1,100 mL) with stirring. The organic phase is separated, washed sequentially with dilute hydrochloric acid and water, dried over anhydrous sodium sulfate and concentrated in vacuo to give a brown, viscous oil (44.5 g) which contains 90% of the title product (83% yield).

EXAMPLE 4

Preparation of 5,7-Dihydroxy-6-(2-chloro-6-fluorophenyl)-1,2,4-triazolo[1,5-a]pyrimidine-

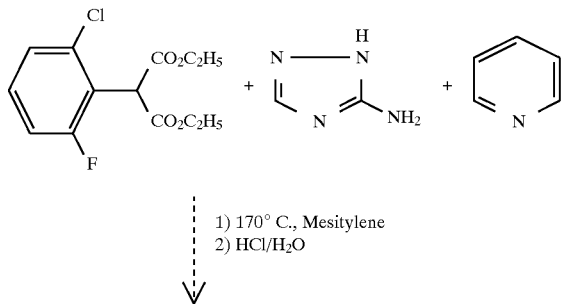

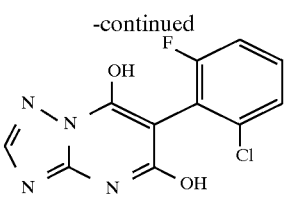

A mixture of diethyl (2-chloro-6-fluorophenyl)malonate (7.3 g, 0.025 mol), 3-amino-1,2,4-triazole (2.1 g, 0.025 mol), mesitylene (20 mL), and pyridine (5 mL) is refluxed for 7 hours at 170° C., cooled to room temperature, and decanted to obtain a solid. A solution of the solid in water (50 mL) is acidified with concentrated hydrochloric acid (5 mL), and the resultant precipitate is collected, washed with water, and dried to give the title product as a solid (5 g, 71% yield, mp 220° C.).

Following essentially the same procedure, but using the appropriate solvent and/or base, 5,7-dihydroxy-6-(2-chloro-6-fluorophenyl)-1,2,4-triazolo[1,5-a]pyrimidine is obtained in the yields shown in Table II.

TABLE II

| Solvent | Base | Temperature °C. | % Yield |
|---|---|---|---|
| mesitylene | sodium hydroxide | 170 | 27 |
| mesitylene | potassium tert-butoxide | 170 | 28 |
| mesitylene | 4-(N,N-dimethylamino)pyridine | 150 | 61 |
| mesitylene | quinoline | 180 | 48 |
| mesitylene | sodium ethoxide | 170 | 55 |
| SHELLSOL ® | pyridine | 180 | 38 |
| no added solvent | pyridine | 160 | 42 |
| no added solvent | N,N,N',N'-tetramethylurea | 170 | 50 |

COMPARATIVE EXAMPLE

Preparation of 5,7-Dihydroxy-6-(2-chloro-6-fluorophenyl)-1,2,4-triazolo[1,5-a]pyrimidine

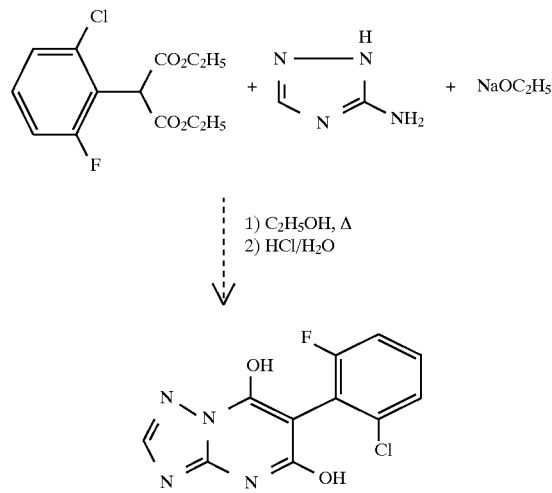

Diethyl (2-chloro-6-fluorophenyl)malonate (108 g, 0.37 mol) and 3-amino-1,2,4-triazole (31.2 g, 0.37 mol) are added to a sodium ethoxide solution (previously prepared by dissolving sodium (8.5 g, 0.37 mol) in ethanol (250 mL)). The resultant reaction mixture is refluxed for 50 hours, cooled to room temperature and filtered to obtain a solid which is washed with diisopropyl ether. A solution of the washed solid in water is acidified with concentrated hydrochloric acid, and the resultant precipitate is collected, washed with water and dried to give the title product as a solid (15.7 g, 14.5% yield, mp 215° C.).

EXAMPLE 5
Preparation of 5,7-Dihydroxy-6-(2-chloro-6-fluorophenyl) benzimidazopyrimidine, 2-aminobenzimidazole salt

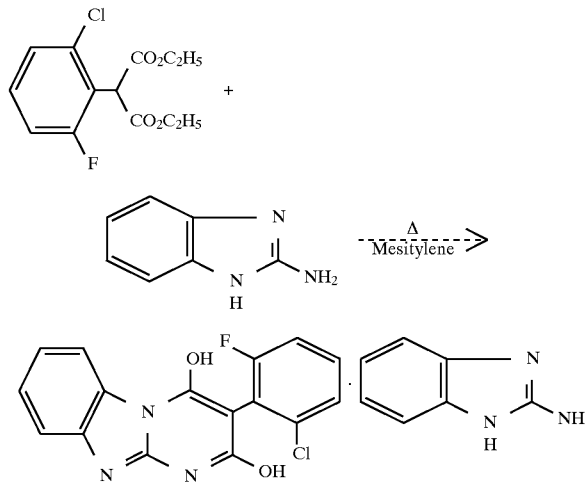

A mixture of diethyl (2-chloro-6-fluorophenyl)malonate (5.8 g, 0.02 mol) and mesitylene is heated to reflux, treated portionwise over 2 hours with 2-aminobenzimidazole (2.7 g, 0.02 mol), refluxed for 4 hours, cooled to room temperature and diluted with acetone. The resultant mixture is filtered to give the title product as white crystals (5.1 g, 55% yield, mp 313°–325° C.).

We claim:
1. A process for the preparation of a compound having the structural formula

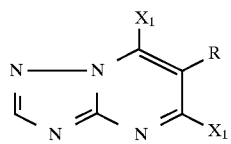

wherein
X$_1$ is chlorine or bromine;
R is phenyl optionally substituted with one or more halogen, nitro, cyano, C$_1$–C$_6$ alkyl, C$_1$–C$_6$ haloalkyl, C$_1$–C$_6$ alkoxy, C$_1$–C$_6$ haloalkoxy, C$_1$–C$_4$ alkoxycarbonyl, phenyl, phenoxy or benzyloxy groups, naphthyl optionally substituted with one or more halogen, nitro, cyano, C$_1$–C$_6$ alkyl, C$_1$–C$_6$ haloalkyl, C$_1$–C$_6$ alkoxy, C$_1$–C$_6$ haloalkoxy, C$_1$–C$_4$ alkoxycarbonyl, phenyl, phenoxy or benzyloxy groups,
hydrogen,
C$_1$–C$_6$ alkyl optionally substituted with one or more halogen, nitro, cyano, C$_1$–C$_4$ alkyl, C$_1$–C$_4$ haloalkyl, C$_1$–C$_4$ alkoxy, C$_1$–C$_4$ haloalkoxy groups,
C$_3$–C$_8$ cycloalkyl optionally substituted with one or more halogen, nitro, cyano, C$_1$–C$_4$ alkyl, C$_1$–C$_4$ haloalkyl, C$_1$–C$_4$ alkoxy, C$_1$–C$_4$ haloalkoxy groups, or
C$_2$–C$_6$ alkenyl optionally substituted with one or more halogen, nitro, cyano, C$_1$–C$_4$ alkyl, C$_1$–C$_4$ haloalkyl, C$_1$–C$_4$ alkoxy, C$_1$–C$_4$ haloalkoxy groups;

which process comprises
(a) reacting (1) a malonic acid ester having the structural formula

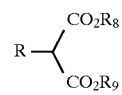

wherein R$^8$ and R$^9$ are each independently C$_1$–C$_6$ alkyl, and R is as described above with (2) an aminotriazole having the structural formula

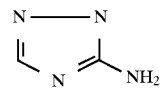

to form an intermediate salt
(b) optionally acidifying said intermediate salt with aqueous acid to form a dihydroxyazolopyrimidine having the structural formula

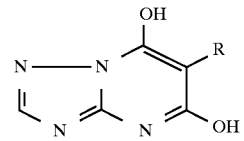

wherein R is as described above, and
(c) halogenating the intermediate salt or dihydroxyazolopyrimidine with at least two equivalents of a halogenating agent,
wherein the reaction between said malonic acid ester and said aminotriazole is carried out at a temperature of 120° to 200° C. in the presence of a tertiary amine base, whereupon an intermediate salt having the structural formula

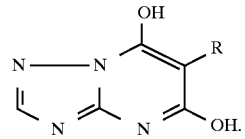

2. The process according to claim 1 wherein said halogenating agent is selected from the group consisting of phosphorus oxychloride, phosphorus oxybromide, phosphorus pentachloride, phosphorus pentabromide and a suitable mixture thereof, and wherein said halogenating step is performed at a temperature of at least about 100° C.
3. The process according to claim 1 wherein said temperature is about 150° C. to 180° C.
4. The process according to claim 1 wherein said base is present in an amount of at least about one molar equivalent relative to said malonic acid ester.
5. The process according to claim 1 wherein said tertiary amine is selected from the group consisting of a tri (C$_2$–C$_6$alkyl)amine, pyridine, a substituted pyridine, quinoline, a substituted quinoline, and N,N,N',N'-tetramethylurea.
6. The process according to claim 5 wherein said tri (C$_2$–C$_6$alkyl)amine is selected from the group consisting of triethylamine, and tributylamine.
7. The process according to claim 1 wherein said malonic acid ester is reacted with said heterocyclylamine in the presence of a solvent.
8. The process according to claim 7 wherein said solvent has a boiling point of about 80° C. to 220° C.

9. The process according to claim 8 wherein said boiling point is about 120° C. to 180° C.

10. The process according to claim 7, wherein said solvent is selected from the group consisting of an aromatic hydrocarbon, a chlorinated aromatic hydrocarbon, a polynuclear aromatic hydrocarbon, an alcohol, and mixtures thereof, and the boiling point of the solvent is at least about 80° C.

11. The process according to claim 10 wherein said aromatic hydrocarbon is selected from the group consisting of mesitylene, toluene, a xylene, and mixtures thereof, said polynuclear aromatic hydrocarbon is selected from the group consisting of naphthalene, an alkylnaphthalene, and mixtures thereof, and said alcohol is butanol.

12. The process according to claim 7 wherein said solvent is mesitylene.

13. The process according to claim 1 wherein said heterocyclylamine is present in an amount of at least about one molar equivalent relative to said malonic acid ester.

14. The process according to claim 1 wherein said aqueous acid is an aqueous mineral acid selected from the group consisting of hydrochloric acid, hydrobromic acid, and sulfuric acid.

15. The process according to claim 1 wherein said halogenation is conducted at a pressure greater than one atmosphere.

16. The process according to claim 1 wherein said halogenating agent is phosphorus oxychloride.

17. The process according to claim 1 wherein said halogenation is conducted at a temperature of about 120° C. to 150° C.

18. The process according to claim 1 wherein
$X_1$ is chlorine;
R is phenyl optionally substituted with one or more halogen, $C_1$–$C_4$alkyl, $C_1$–$C_4$haloalkyl, $C_1$–$C_4$alkoxy, $C_1$–$C_4$haloalkoxy, phenyl, phenoxy or benzyloxy groups, or
naphthyl.

19. The process according to claim 18 wherein
R is phenyl optionally substituted with one or more halogen, $C_1$–$C_4$alkyl, $C_1$–$C_4$haloalkyl, $C_1$–$C_4$alkoxy or $C_1$–$C_4$haloalkoxy groups;
X is N; and
Y is CH.

20. A process for the preparation of a compound having the structural formula

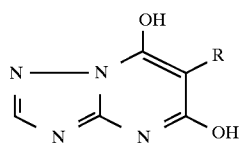

wherein
R is phenyl optionally substituted with one or more halogen, nitro, cyano, $C_1$–$C_6$ alkyl, $C_1$–$C_6$ haloalkyl, $C_1$–$C_6$ alkoxy, $C_1$–$C_6$ haloalkoxy, $C_1$–$C_4$alkoxycarbonyl, phenyl, phenoxy or benzyloxy groups,
naphthyl optionally substituted with one or more halogen, nitro, cyano, $C_1$–$C_6$ alkyl, $C_1$–$C_6$ haloalkyl, $C_1$–$C_6$ alkoxy, $C_1$–$C_6$ haloalkoxy, $C_1$–$C_4$ alkoxycarbonyl, phenyl, phenoxy or benzyloxy groups,
hydrogen,
$C_1$–$C_6$ alkyl optionally substituted with one or more halogen, nitro, cyano, $C_1$–$C_4$ alkyl, $C_1$–$C_4$ haloalkyl, $C_1$–$C_4$ alkoxy, $C_1$–$C_4$ haloalkoxy groups, $C_3$–$C_8$ cycloalkyl optionally substituted with one or more halogen, nitro, cyano, $C_1$–$C_4$ alkyl, $C_1$–$C_4$ haloalkyl, $C_1$–$C_4$ alkoxy, $C_1$–$C_4$ haloalkoxy groups, or
$C_2$–$C_6$ alkenyl optionally substituted with one or more halogen, nitro, cyano, $C_1$–$C_4$ alkyl, $C_1$–$C_4$ haloalkyl, $C_1$–$C_4$ alkoxy, $C_1$–$C_4$ haloalkoxy groups;
which process comprises
(a) reacting (1) a malonic acid ester having the structural formula

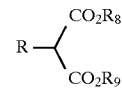

wherein $R^8$ and $R^9$ are each independently $C_1$–$C_6$ alkyl, and R is as described above with (2) an aminotriazol having the structural formula

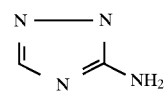

at a temperature of 120° to 200° C. in the presence of a base, to form an intermediate salt, and
(b) acidifying said intermediate salt with aqueous acid; wherein the reaction between said malonic acid ester and said aminotriazol is carried out at a temperature of 120° to 200° C. in the presence of a tertiary amine base, whereupon an intermediate salt having the structural formula

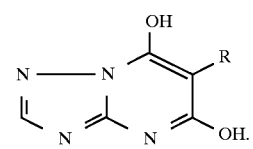

21. The process according to claim 20 wherein said temperature is about 150° C. to 180° C.

22. The process according to claim 20 wherein said base is present in an amount of at least about one molar equivalent relative to the malonic acid ester.

23. The process according to claim 20 wherein the tertiary amine is selected from the group consisting of a tri($C_2$–$C_6$alkyl)amine, pyridine, a substituted pyridine, quinoline, a substituted quinoline, and N,N,N',N'-tetramethylurea.

24. The process according to claim 23 wherein the tri($C_2$–$C_6$alkyl)amine is selected from the group consisting of triethylamine, and tributylamine.

25. The process according to claim 20 wherein the malonic acid ester is reacted with the heterocyclylamine in the presence of a solvent.

26. The process according to claim 25 wherein the boiling point of said solvent is about 80° C. to 220° C.

27. The process according to claim 25 wherein said boiling point is about 120° C. to 180° C.

28. The process according to claim 25 wherein said solvent is selected from the group consisting of an aromatic hydrocarbon, a chlorinated aromatic hydrocarbon, a polynuclear aromatic hydrocarbon, an alcohol, and mixtures thereof, and the boiling point of said solvent is at least about 80° C.

29. The process according to claim 28 wherein said aromatic hydrocarbon is selected from the group consisting of mesitylene, toluene, a xylene, and mixtures thereof, said polynuclear aromatic hydrocarbon is selected from the group consisting of naphthalene, an alkylnaph-thalene, and mixtures thereof, and said alcohol is butanol.

30. The process according to claim 25 wherein said solvent is mesitylene.

31. The process according to claim 20 wherein said heterocyclylamine is present in an amount of at least about one molar equivalent relative to said malonic acid ester.

32. The process according to claim 20 wherein said aqueous acid is an aqueous mineral acid selected from the group consisting of hydrochloric acid, hydrobromic acid, and sulfuric acid.

33. The process according to claim 20 wherein

R is phenyl optionally substituted with one or more halogen, $C_1$–$C_4$alkyl, $C_1$–$C_4$haloalkyl, $C_1$–$C_4$alkoxy, $C_1$–$C_4$haloalkoxy, phenyl, phenoxy or benzyloxy groups, or naphthyl.

34. The process according to claim 33 wherein

R is phenyl optionally substituted with one or more halogen, $C_1$–$C_4$alkyl, $C_1$–$C_4$haloalkyl, $C_1$–$C_4$alkoxy or $C_1$–$C_4$haloalkoxy groups;

X is N; and

Y is CH.

* * * * *